US006402679B1

(12) United States Patent
Mortier et al.

(10) Patent No.: US 6,402,679 B1
(45) Date of Patent: Jun. 11, 2002

(54) EXTERNAL STRESS REDUCTION DEVICE AND METHOD

(75) Inventors: Todd J. Mortier, Minneapolis; Cyril J. Schweich, Jr., St. Paul; Robert M. Vidlund, Maplewood; Peter T. Keith, St. Paul; Thomas M. Paulson; David A. Kusz, both of Minneapolis, all of MN (US)

(73) Assignee: Myocor, Inc., St. Paul, MN (US)

( * ) Notice: Subject to any disclaimer, the term of this patent is extended or adjusted under 35 U.S.C. 154(b) by 0 days.

(21) Appl. No.: 09/711,501

(22) Filed: Nov. 14, 2000

Related U.S. Application Data

(63) Continuation of application No. 09/157,486, filed on Sep. 21, 1998, now Pat. No. 6,183,411.

(51) Int. Cl.[7] .............................. A61F 1/00; A61B 17/12
(52) U.S. Cl. ............................. 600/16; 600/37; 623/301
(58) Field of Search .............................. 600/16–18, 37; 128/897; 623/3, 11

(56) References Cited

U.S. PATENT DOCUMENTS

| 4,192,293 A | 3/1980 | Asrican ..................... 600/18 |
| 4,261,342 A | 4/1981 | Aranguren Duo ............. 128/1 |
| 4,372,293 A | 2/1983 | Vijil-Rosales |
| 4,409,974 A | 10/1983 | Freedland ................... 128/92 |
| 4,536,893 A | 8/1985 | Parravicini .................. 623/3 |

(List continued on next page.)

FOREIGN PATENT DOCUMENTS

| DE | 36 14 292 | * | 11/1987 |
| DE | 42 34 127 | * | 5/1994 |
| DE | 296 19 294 | * | 7/1997 |
| DE | 199 47 885 A1 | * | 4/2000 |
| EP | 0 583 012 A1 | * | 2/1994 |

(List continued on next page.)

OTHER PUBLICATIONS

Carpentier et al., "Myocardial Substitution with a Stimulated Skeletal Muscle: First Successful Clinical Case," Letter to the Editor, p. 1267, Sep. 25, 1996.*

Ianuzzo et al., "Preservation of the Latissim us Dorsi Muscle During Cardiomyoplasty Surgery," *J. Card. Surg.*, 1996:11:99–108.*

Ianuzzo et al., "On Preconditioning of Skeletal Muscle: Application to Dynamic Cardiomyoplasty," Invited Commentary, *J. Card. Surg.*, 1996:11:109–110.*

Chachques et al., "Latissimus Dorsi Dynamic Cardiomyoplasty," *Ann. Thorac. Surg.*, 1989:47:600–604.*

Moreira et al., "Latissimus Dorsi Cardiomyoplasty in the Treatment of Patients with Dilated Cardiomyopathy," Supplement IV Circulation, Sep. 25, 1996, 7 pgs.*

Lucas et al., "Long–Term Follow–Up (12 to 35 Weeks) After Dynamic Cardiomyoplasty," *JACC*, vol. 22, No. 3, Sep. 1993:758–67.

Batista et al., "Partial Left Ventriculectom y to Improve Left Ventricular Function in End–Stage Heart Disease," *J. Card. Surg.*, 1996:11:96–98.

"Congestiv e Heart Failure in the United States: A New Epidemic" Data Fact Sheet, National Heart, Lung, and Blood Institute, National Institutes of Health, Dec. 9, 1996, pp. 1–6.

Kormos et al., "Experience with Univentricular Support in Mortally Ill Cardiac Transplant Candidates," *Ann. Thorac. Surg.*, 1990:49:261–71.

(List continued on next page.)

*Primary Examiner*—Jeffrey R. Jastrzab
(74) *Attorney, Agent, or Firm*—Finnegan, Henderson, Farabow, Garrett & Dunner, LLP

(57) ABSTRACT

An external heart wall stress reduction apparatus is provided to create a heart wall shape change. The device is generally disposed to the exterior of a heart chamber to reshape the chamber into a lower stress configuration.

10 Claims, 13 Drawing Sheets

U.S. PATENT DOCUMENTS

| | | | |
|---|---|---|---|
| 4,690,134 A | 9/1987 | Snyders | |
| 4,705,040 A | 11/1987 | Mueller et al. | |
| 4,936,857 A | 6/1990 | Kulik | |
| 4,944,753 A | 7/1990 | Burgess et al. | 623/16 |
| 4,960,424 A | 10/1990 | Grooters | 623/2 |
| 4,997,431 A | 3/1991 | Isner et al. | 606/15 |
| 5,106,386 A | 4/1992 | Isner et al. | 606/15 |
| 5,131,905 A | 7/1992 | Grooters | 600/16 |
| RE34,021 E | 8/1992 | Mueller et al. | 604/51 |
| 5,169,381 A | 12/1992 | Snyders | 600/16 |
| 5,192,314 A | 3/1993 | Daskalakis | 623/3 |
| 5,250,049 A | 10/1993 | Michael | 606/72 |
| 5,284,488 A | 2/1994 | Sideris | 606/213 |
| 5,385,528 A | 1/1995 | Wilk | 600/18 |
| 5,433,727 A | 7/1995 | Sideris | 606/213 |
| 5,450,860 A | 9/1995 | O'Connor | |
| 5,452,733 A | 9/1995 | Sterman et al. | 128/898 |
| 5,458,574 A | 10/1995 | Machold et al. | 604/101 |
| 5,496,305 A | 3/1996 | Kittrell et al. | 606/15 |
| 5,509,428 A | 4/1996 | Dunlop | 128/898 |
| 5,533,958 A | 7/1996 | Wilk | 600/18 |
| 5,571,215 A | 11/1996 | Sterman et al. | 623/66 |
| 5,584,803 A | 12/1996 | Stevens et al. | 604/4 |
| 5,593,424 A | 1/1997 | Northrup, III | |
| 5,665,092 A | 9/1997 | Mangiardi et al. | |
| 5,682,906 A | 11/1997 | Sterman et al. | 128/898 |
| 5,702,343 A | 12/1997 | Alferness | 607/37 |
| 5,718,725 A | 2/1998 | Sterman et al. | 623/2 |
| 5,758,663 A | 6/1998 | Wilk et al. | |
| 5,800,334 A | 9/1998 | Wilk | |
| 5,800,528 A | 9/1998 | Lederman et al. | 623/3 |
| 5,814,097 A | 9/1998 | Sterman et al. | 623/2 |
| 5,849,005 A | 12/1998 | Garrison et al. | 606/1 |
| 5,855,210 A | 1/1999 | Sterman et al. | 128/898 |
| 5,855,614 A | 1/1999 | Stevens et al. | 623/11 |
| 5,865,791 A | 2/1999 | Whayne et al. | |
| 5,902,229 A | 5/1999 | Tsitlik et al. | |
| 5,957,977 A | 9/1999 | Melvin | |
| 5,961,440 A | 10/1999 | Schweich, Jr. et al. | |
| 5,971,910 A | 10/1999 | Tsitlik et al. | |
| 5,971,911 A | 10/1999 | Wilk | |
| 5,972,022 A | 10/1999 | Huxel | |
| 5,984,857 A | 11/1999 | Buck et al. | |
| 6,024,096 A * | 2/2000 | Buckberg | |
| 6,024,756 A | 2/2000 | Huebsch et al. | |
| 6,045,497 A | 4/2000 | Schweich, Jr. et al. | |
| 6,050,936 A | 4/2000 | Schweich, Jr. et al. | |
| 6,059,715 A | 5/2000 | Schweich, Jr. et al. | |
| 6,071,303 A * | 6/2000 | Laufer | |
| 6,077,214 A * | 6/2000 | Mortier et al. | |
| 6,077,218 A * | 6/2000 | Alferness | |
| 6,079,414 A * | 6/2000 | Roth | |
| 6,085,754 A * | 7/2000 | Alferness et al. | |
| 6,095,968 A | 8/2000 | Snyders | |
| 6,110,100 A * | 8/2000 | Talpade | |
| 6,117,159 A * | 9/2000 | Huebsch et al. | |
| 6,123,662 A * | 9/2000 | Alferness et al. | |
| 6,125,852 A * | 10/2000 | Stevens et al. | |
| 6,126,590 A * | 10/2000 | Alferness | |
| 6,155,968 A * | 12/2000 | Wilk | |
| 6,155,972 A * | 12/2000 | Nauertz et al. | |
| 6,162,168 A * | 12/2000 | Schweich, Jr. et al. | |
| 6,165,119 A | 12/2000 | Schweich, Jr. et al. | |
| 6,165,120 A | 12/2000 | Schweich, Jr. et al. | |
| 6,165,121 A | 12/2000 | Alferness | |
| 6,165,122 A | 12/2000 | Alferness | |
| 6,169,922 B1 | 1/2001 | Alferness et al. | |
| 6,174,279 B1 | 1/2001 | Girard | |
| 6,179,791 B1 | 1/2001 | Krueger | |
| 6,190,408 B1 * | 2/2001 | Melvin | |
| 6,193,648 B1 | 2/2001 | Krueger | |
| 6,260,820 B1 * | 3/2001 | Kazi et al. | |
| 6,221,103 B1 * | 4/2001 | Melvin | |
| 6,221,104 B1 | 4/2001 | Buckberg et al. | |
| 6,224,540 B1 | 5/2001 | Lederman et al. | |
| 6,230,714 B1 | 5/2001 | Alferness et al. | |
| 6,238,334 B1 | 5/2001 | Easterbrook, III et al. | |
| 6,241,654 B1 * | 6/2001 | Alferness | |
| 6,258,021 B1 * | 7/2001 | Wilk | |

FOREIGN PATENT DOCUMENTS

| | | |
|---|---|---|
| WO | 91/19465 * | 12/1991 |
| WO | 95/06447 * | 3/1995 |
| WO | 95/16476 * | 9/1995 |
| WO | 96/04852 A1 * | 2/1996 |
| WO | 96/40356 * | 12/1996 |
| WO | 97/24101 * | 7/1997 |
| WO | 98/03213 | 1/1998 |
| WO | 98/14136 * | 4/1998 |
| WO | 98/18393 | 5/1998 |
| WO | 9826738 | 6/1998 |
| WO | 98/29041 * | 7/1998 |
| WO | 98/32382 | 7/1998 |
| WO | 99/11201 * | 3/1999 |
| WO | 99/13777 * | 3/1999 |
| WO | 99/30647 * | 6/1999 |
| WO | 99/44534 * | 9/1999 |
| WO | 99/44680 * | 9/1999 |
| WO | 99/52470 * | 10/1999 |
| WO | 99/56655 * | 11/1999 |
| WO | 00/02500 * | 1/2000 |
| WO | 00/06026 * | 2/2000 |
| WO | 00/06028 * | 2/2000 |
| WO | 00/13722 * | 3/2000 |
| WO | 00/18320 * | 4/2000 |
| WO | 00/27304 * | 5/2000 |
| WO | 00/28912 * | 5/2000 |
| WO | 00/28918 * | 5/2000 |
| WO | 00/36995 * | 6/2000 |
| WO | 00/42919 * | 7/2000 |
| WO | 00/45735 * | 8/2000 |
| WO | 00/61033 * | 10/2000 |
| WO | 00/62727 * | 10/2000 |
| WO | 01/03608 A1 * | 1/2001 |
| WO | 01/21070 * | 3/2001 |
| WO | 01/21098 * | 3/2001 |
| WO | 01/21099 A1 * | 3/2001 |
| WO | 01/50981 A1 * | 7/2001 |

OTHER PUBLICATIONS

Wampler et al., "Treatment of Cardiogenic Shock with the Hemopump Left Ventricular Assist Device," *Ann. Thorac. Surg.*, 1991:52:506–13.

McCarthy et al., "Clinical Experience with the Novacor Vetricular Assist System," *J. Thorac. Cardiovasc. Surg.*, 1991:102–578–87.

Burnett et al., "Improved Survival After Hemopump Insertion in Patients Experiencing Postcardiotomy Cardiogenic Shock During Cardiopulmonary Bypass," From the Section of Transplantation, Division of Cardiovascular Surgery, Texas Heart Institute and St. Luk e's Episcopal Hospital, Houston, Tex as, dated even with or prior to Jan. 2, 1997, pp. 626–628.

Phillips et al., "Hemopump Support for the Failing Heart," From the Department of Cardiovascular Medicine and Surgery, Mercy Hospital Medical Center, Des Moines, Iowa, date even with or prior to Jan. 2, 1997, pp. 629–631.

Deeb et al., "Clinical Ex perience with the Nim bus Pump," From the University of Michigan Medical Center Section of Thoracic Surgery and Division of Cardiology, Ann Arbor, Michigan, date ev en with or prior to Jan. 2, 1997, pp. 632–636.

Bearnson et al., "Development of a Prototype Magnetically Suspended Rotor Ventricular Assist Device," ASAIO Journal, 1996, pp. 275–280.

Sakakibara et al., "A Muscle Powered Cardiac Assist Dev ice for Right Ventricular Support: Total Assist or Partial Assist?," Trans. Am .Soc. Artif. Intern. Organs, vol. XXXVI, 1990, pp. 372–375.

Medtronic, Inc. 1996 Annual Shareholders Report, 79 pages.

ABIOMED, Inc. Annual Report 1996, 32 pages.

Press Release dated Sep. 16, 1996, "ABIOMED Wins $8.5 Million Federal Contract to Qualify its Artificial Heart for Human Trials," 5 pages.

Press Release dated Sep. 26, 1996, "ABIOMED's Tem porary Artificial Heart Sy stem Reaches 200 U.S. Medical Center M ilestone," 1 page.

Press Release dated M ay 17, 1996, "ABIO MED Receiv es FDA Approv al to Expand Indications for Use of Cardiac Assist Sy stem," 1 page.

Press Release dated O ct. 3, 1995, "ABIOMED Wins $4.35 Million Contract from the National Heart, Lung and Blood Institutes to Dev elop Implantable Heart Booster," 1 page.

Press Release dated Sep. 29, 1995, "ABIOMED" Wins NIH Grant to Develop Calcification–Resistant Plastic Heart Valve, 1 page.

Press Release dated Aug. 25, 1995, "ABIOMED Wins Research G rant from NIH to Dev elop Suturing Instrument for Abdom inal Surgery," 1 page.

Press Release dated Aug. 11, 1995, "ABIOMED Receiv es Grant from NIH to Develop Disposable Bearingless Cen-trifugal Blood Pum p," 1 page.

Press Release dated Jun. 9, 1995, "ABIOMED Receiv es Grant from National Institutes of Health to Develop a Laser Welding Technique for Tissue Repair," 1 page.

Press Release dated Apr. 27, 1995, "ABIOMED's Tempo-rary Artificial Heart System Reaches 1,000 Patient Mile-stone; BVS–5000 in More Than 100 U.S. Medical Centers," 1 page.

"Reversible Cardiomyopathy," Thoratec's Heartbeat, vol. 10.2, Aug. 1996, 4 pages.

Tsai et al., "Surface Modifying Additives for Improved Device–Blood Compatibility," ASAIO Journal, 1994, pp. 619–624.

Farrar et al., "A New Skeletal Muscle Linear–Pull Energy Convertor as a Power Source f or Prosthetic Support Devices," The Journal of Heart & Lung Transplantation , vol. 11, No. 5, Sep., 1992, pp. 341–349.

Brochure entitled "Thoratec Ventricular Assist Dev ice Sys-tem—Because Heart Patients Come in All Sizes," date even with or prior to Jan. 2, 1997, 5 pages.

Press Release dated O ct. 3, 1994, "Heartmate System Becomes First Implantable Cardiac–Assist Device to be Approved for Commercial Sale in the U.S.," 2 pages.

Bocchi et al., "Clinical Outcome after Surgical Remodeling of Left Ventricle in Candidates to Heart Transplantation with Idiopathic Dilated Cardiomypathy—Short Term Results," date even with or prior to Jan. 2, 1997, 1 page.

Bach et al., "Early Improvement in Congestive Heart Failure after Correction of Secondary Mitral Regurgitation in End–Stage Cardiomyopathy," American Heart Journal , Jun. 1995, pp. 1165–1170.

Schuler et al., "Temporal Response of Left Ventricular Performance to Mitral Valve Surgery," vol. 59, No. 6, Jun. 1979, pp. 1218–1231.

Huikuri, "Effect of Mitral Valv e Replacem ent on Left Ventricular Function in Mitral Regurgitation," Br. Heart J., vol. 49, 1983, pp. 328–333.

Pitarys II et al., "Long–Term Effects of Excision of the Mitral Apparatus on G lobal And Regional Ventricular Function in Hum ans," JACC, vol. 15, No. 3, M ar. 1, 1990, pp. 557–563.

Bolling et al., "Surgery for Acquired Heart Disease/Early Outcome of Mitral Valve Reconstruction in Patients with End–Stage Cardiomyopathy," The Journal of Thoracic and Carciovascular Surgery, vol. 109, No. 4, Apr. 1995, pp. 676–683.

Masahiro et al., "Surgery for Acquired Heart Disease/Effects of Preserving Mitral Apparatus on Ventricular Systolic Function in Mitral Valve Operations in Dogs," The Journal of Thoracic and Cardiovascular Surgery, vol. 106, No. 6, Dec. 1993, pp. 1138–1146.

Dick stein et al., "Heart Reduction Surgery : An Analysis of the Impact on Cardiac Function," The Journal of Thoracic and Carciovascular Surgery, vol. 113, No. 6, Jun. 1997, 9 pages.

McCarthy et al., "Early Results with Partial Left Ventri-culectomy," From the Departments of Thoracic and Cardio-vascular Surgery , Cardiology , and Transplant Center, Cleveland Clinic Foundation, Presented at the 77$^{th}$ Annual Meeting of the American Association of Thoracic Surgeons, May 1997, 33 pages.

Alonso–Lej, M.D., "Adjustable Annuloplasty for Tricuspid Insufficiency," The Annals of Thoracic Surgery, vol. 46, No. 3, Sep. 1988, 2 pages.

Kurlansky et al., "Adjustable Annuloplasty for Tricuspid Insufficiency," Ann. Thorac. Surg., 44:404–406, Oct. 1987.

Boyd et al., "Tricuspid Annuloplasty ," The Journal of Thoracic Cardiovascular Surgery, vol. 68, No. 3, Sep. 1974, 8 pages.

Edie, M.D. et al., "Surgical repair of single ventricle,"The Journal of Thoracic and Cardiovascular Surgery, vol. 66, No. 3, Sep., 1973, pp. 350–360.

McGoon, M.D. et al., "Correction of the univentricular heart having tWIPO atrioventricular valves," The Journal of Tho-racic and Carciovascular Surgery, vol. 74, No. 2, Aug., 1977, pp. 218–226.

Lev, M.D., et al., "Single (Primitive) Ventricle," Circulation , vol. 39, May, 1969, pp. 577–591.

Westaby with Bosher, "Landmarks in Cardiac Surgery ," 1997, pp. 198–199.

Shumacker, "Cardiac Aneurysms," The Evolution of Car-diac Surgery, 1992, pp. 159–165.

Feldt, M.D., "Current status of the septation procedure f or univentricular heart," The Journal of Thoracic and Cardiov ascular Surgery, vol. 82, No. 1, Jul., 1981, pp. 93–97.

Doty, M.D., "Septation of the univentricular heart," The Journal of Thoracic and Cardiovascular Surgery, vol. 78, No. 3, Sep., 1979, pp. 423–430.

Savage, M.D., "Repair of left ventricular aneurysm," The Journal of Thoracic and Cardiovascular Surgery, vol. 104, No. 3, Sep., 1992, pp. 752–762.

Cox, "Left Ventricular Aneurysms: Pathophy siologic Observations and Standard Resection," *Seminars in Thoracic and Carciovascular Surgery*, vol. 9, No. 2, Apr., 1997, pp. 113–122.

Melvin, "Ventricular Radius Reduction Without Resection: A Computational Analysis," *ASAIO Journal*, 45:160–165, 1999.

McCarthy, Transcription of Mar. 13, 2000 Presentation.* acorn cardiovascular, inc., "Acorn Cardiovascular Abstracts", Nov. 13, 2000.* acorn cardiovascular, inc., "Acorn Cardiovascular Summary", undated.*

Nation's First "Heart Jacket" Surgery to Treat Heart Failure Performed at HUP: Novel "Cardiac Support Device" Comes to America After Promising Results in Europe, Jun. 26, 2000.* acorn cardiovascular, inc., Acorn Cardiovascular Company Overview, Jun. 2000.* acorn cardiovascular, inc., "Acorn Cardiovascular Company Overview", undated.* acorn cardiovascular, inc., Acorn Cardiovascular Business Plan, May 2000.* acorn cardiovascular, inc., "Acorn Cardiovascular Highlights Abstracts", Mar. 10, 1999.* acorn cardiovascular, inc., "Acorn Cardiovascular Highlights Abstracts", Apr. 19, 1999.* acorn cardiovascular, inc., "Acorn Cardiovascular Highlights Abstracts", Oct. 1, 1999.* acorn cardiovascular, inc., "Acorn Cardiovascular Highlights Abstracts", Nov. 9, 1999.*

Batista et al., "Partial Left Ventriculectomy to Treat End-Stage Heart Disease", *Ann. Thorac. Surg.*, 64:634–8, 1997.*

Melvin, "Ventricular Radius–Reduction Without Resection a Computational Assessment", undated.*

Melvin et al., Reduction of Ventricular Wall Tensile Stress by Geometric Remodeling Device, 1999.*

Kay et al., "Surgical Treatment of Mitral Insufficiency", *The Journal of Thoracic Surgery*, 29: 618–620, 1955.

Kay et al., "Surgical Treatment of Mitral Insufficiency", *Surgery*, 37:697–706, May 1955.

Bailey et al."The Surgical Correction of Mitral Insufficiency By The Use of Pericardial Grafts", *The Journal of Thoracic Surgery*, 28:551–603, Dec. 1954.

Harken et al., "The Surgical Correction of Mitral Insufficiency", *The Journal of Thoracic Surgery*, 28:604–27, 1954.

Shumacker, Jr., "Attempts to Control Mitral Regurgitation", *The Evolution of Cardiac Surgery*, 203–210, 1992.

"Heart 'jacket' could help stop heart failure progression", *Clinica* 916:15, Jul. 2000.

McCarthy et al., Device Based Left Ventricular Shape Change Immediately Reduces Left Ventricular Volume and Increases Ejection Fraction in a Pacing Induced Cardiomyopathy Model in Dogs: A Pilot Study , *JACC*, 838–3, Feb. 2000.

Harken et al., "The Surgical Correction of Mitral Insufficiency", *Surgical Forum*, 4:4–7, 1953.

Bailey et al., "Closed Intracardiac Tactile Surgery", *Diseases of the Chest*, 22:1–24, Jul. 1952.

Sakakibara, "A Surgical Approach to the Correction of Mitral Insufficiency", *Annals of Surgery*, 142:196–203, 1955.

Glenn et al., "The Surgical Treatment of Mitral Insufficiency: The Fate of A Vascularized Transchamber Intracardiac G raft", *Annals of Surgery*, 141:510–518, Apr. 1955.

* cited by examiner

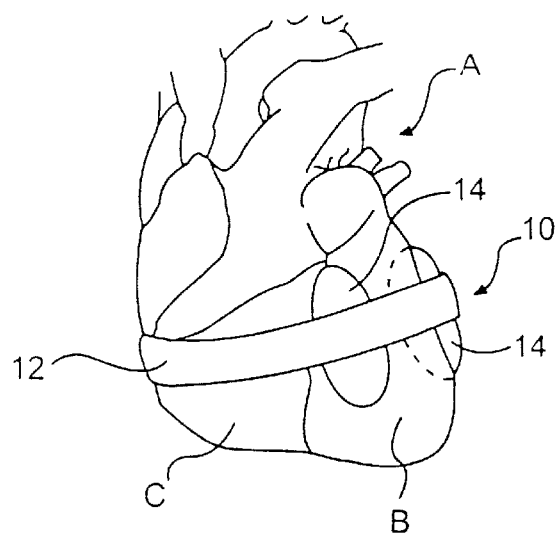
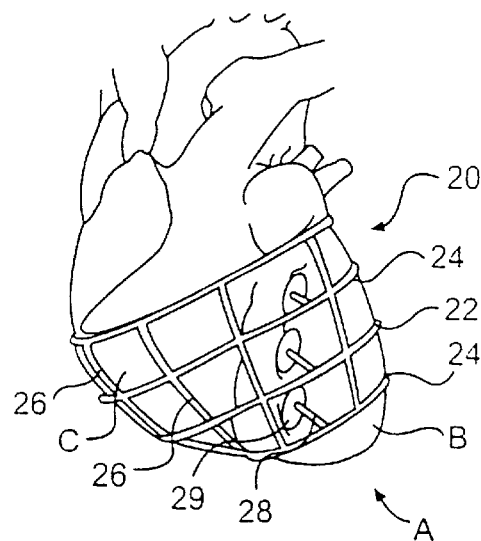
FIG. 1          FIG. 3
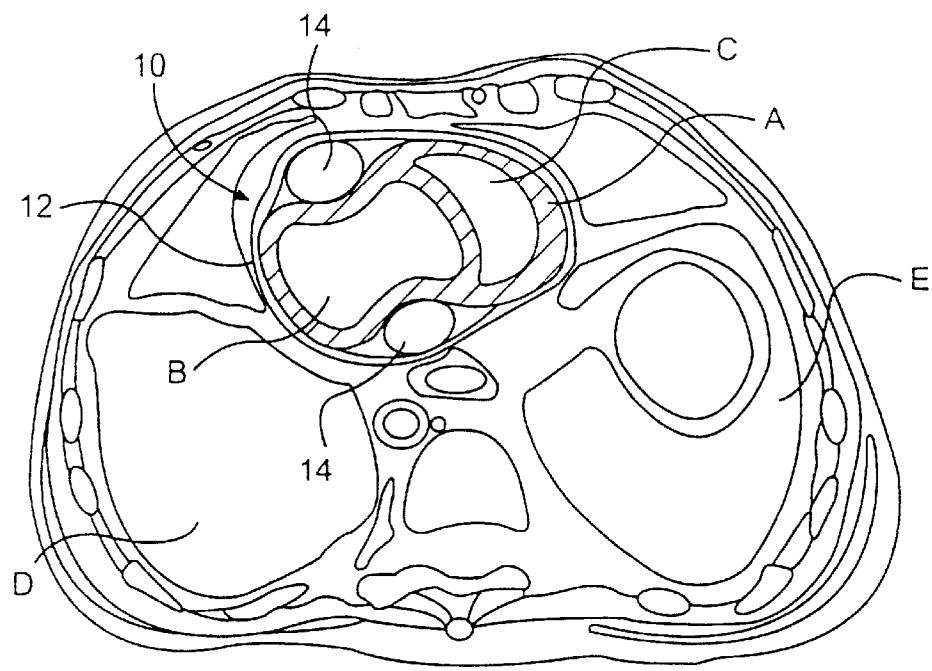
FIG. 2

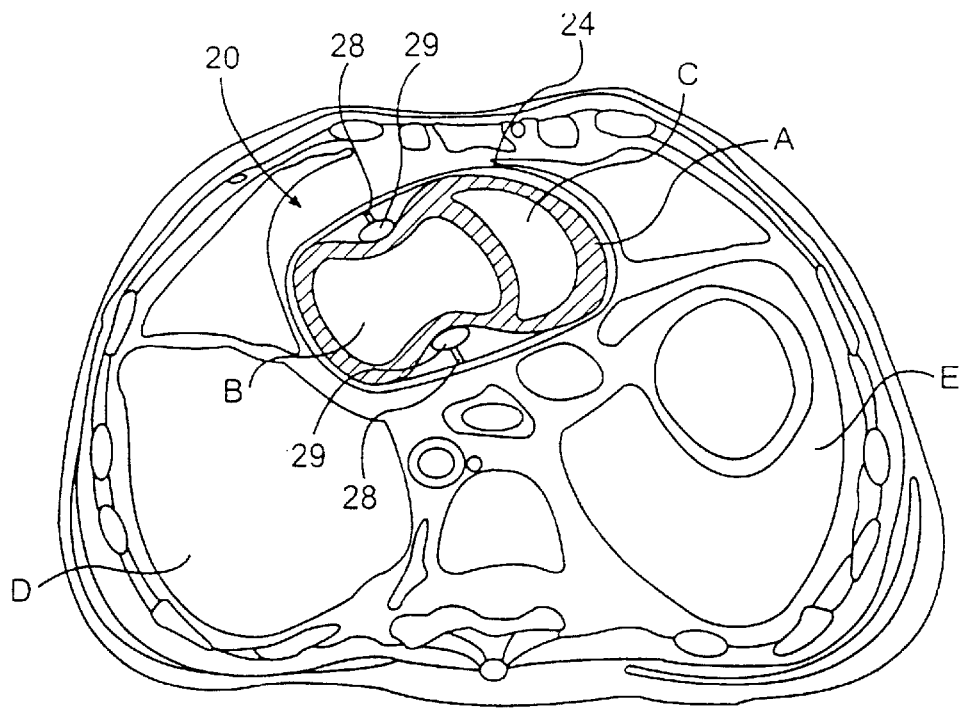
FIG. 4
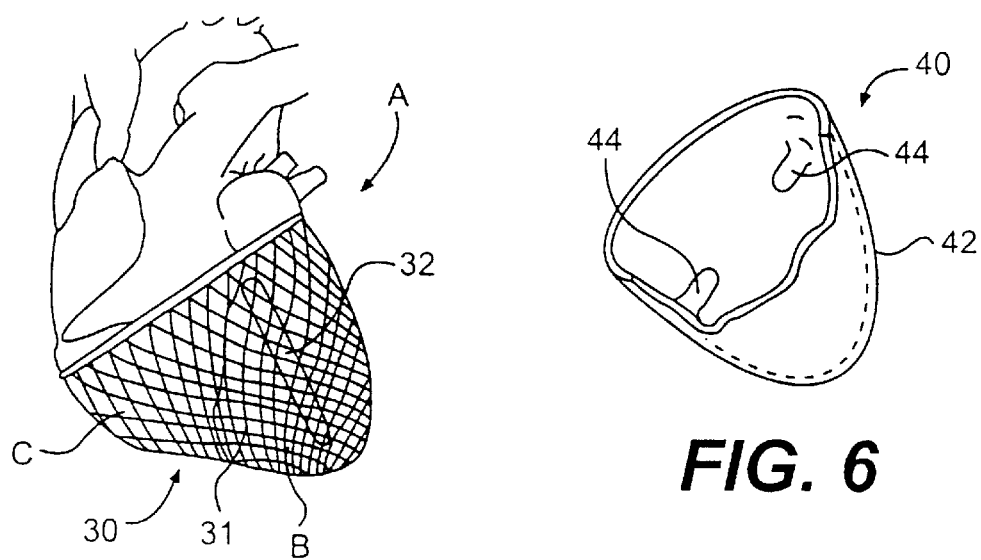
FIG. 5
FIG. 6

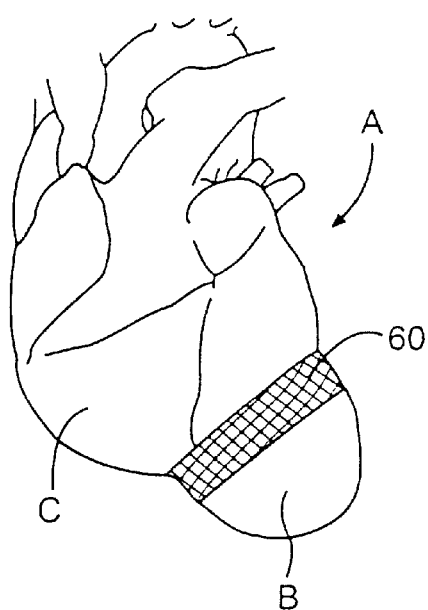
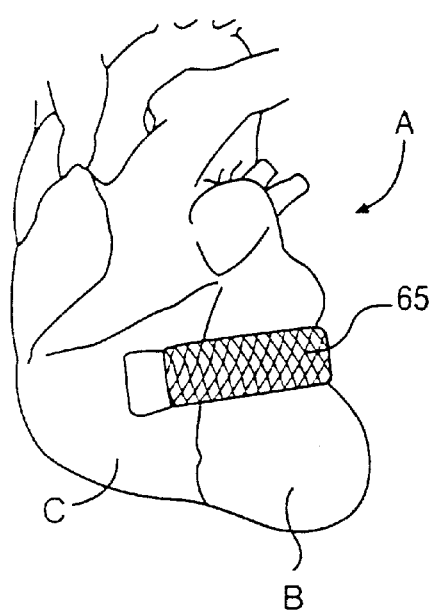
FIG. 10   FIG. 11
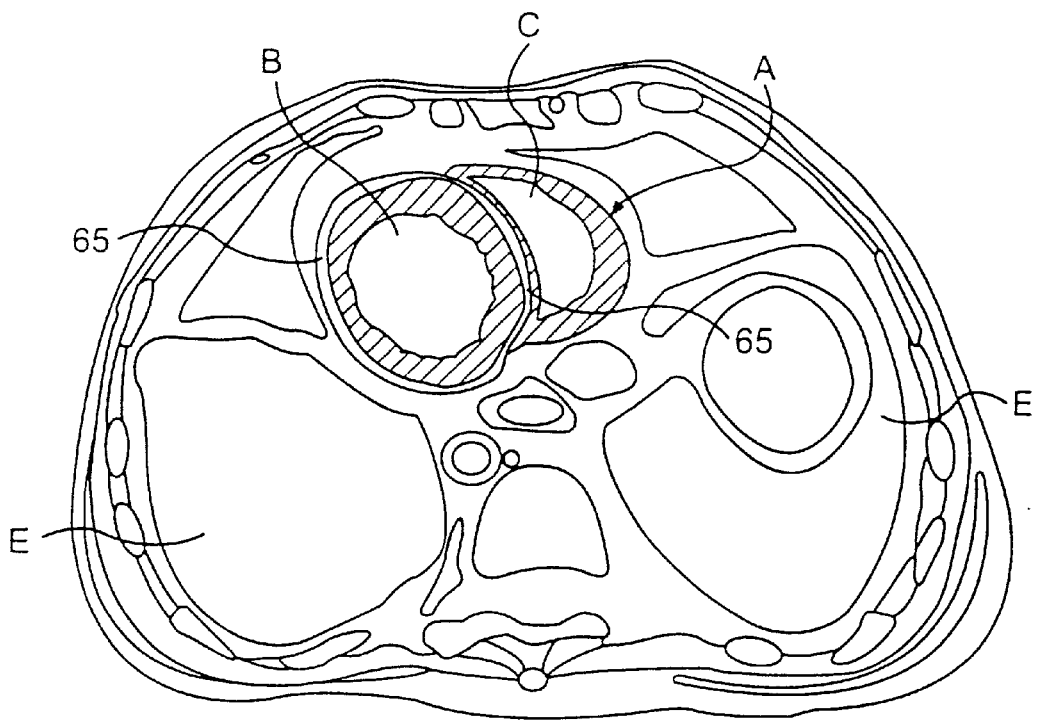
FIG. 12

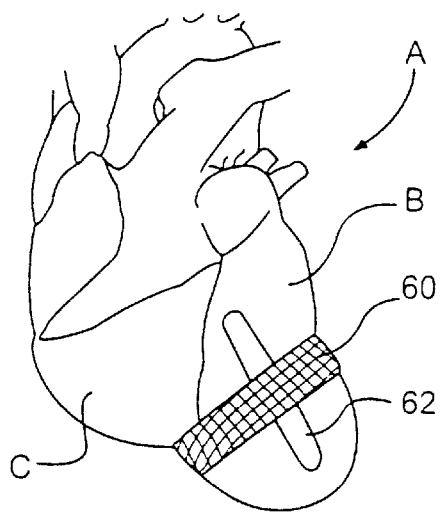
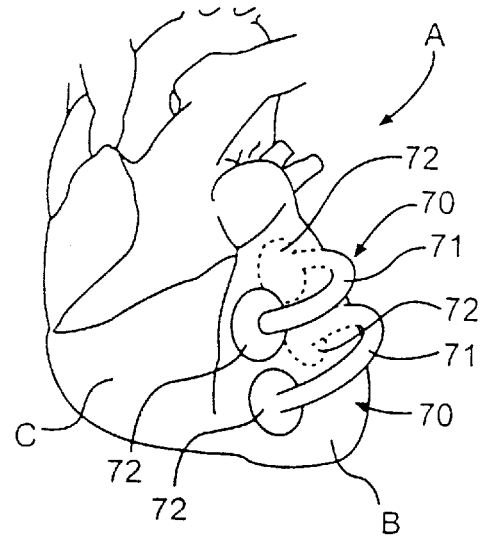
FIG. 13  FIG. 14
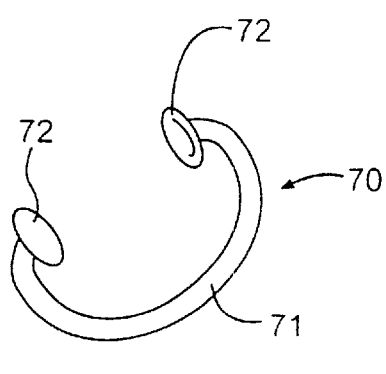
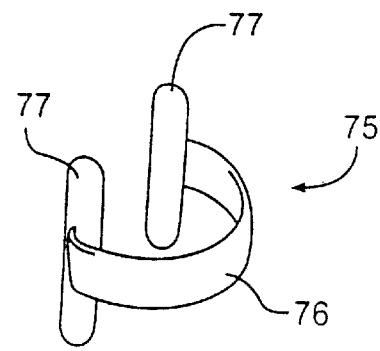
FIG. 15  FIG. 16

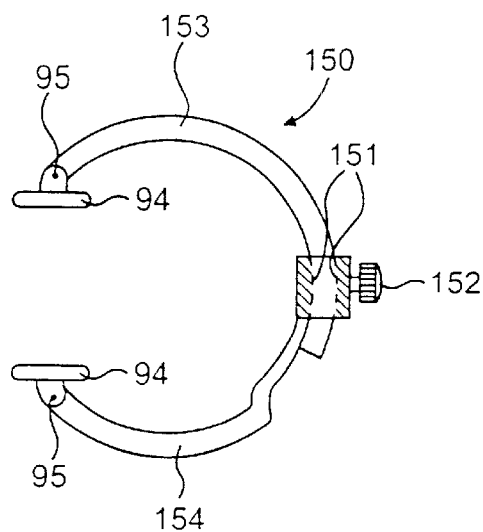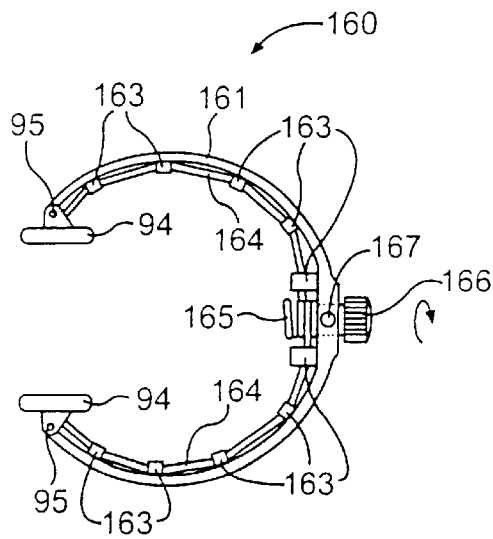
FIG. 25  FIG. 26
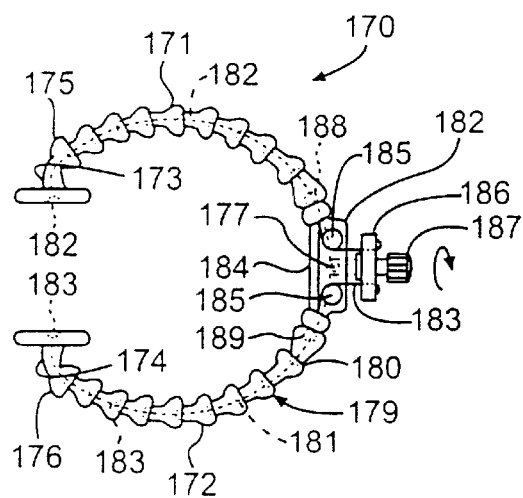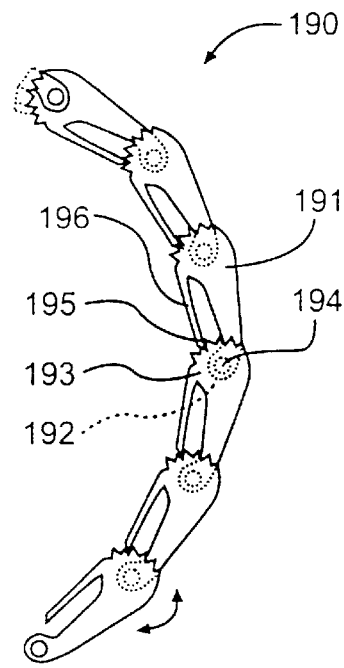
FIG. 27  FIG. 28

EXTERNAL STRESS REDUCTION DEVICE AND METHOD

This is a continuation of application Ser. No. 09/157,486, filed Sep. 21, 1998 now U.S. Pat. No. 6,183,411, which is incorporated herein by reference.

FIELD OF THE INVENTION

The present invention pertains to the field of heart failure in devices and methods for treatment thereof.

BACKGROUND OF THE INVENTION

The syndrome of heart failure is a common course for the progression of many forms of heart disease. Heart failure may be considered to be the condition in which an abnormality of cardiac function is responsible for the inability of the heart to pump blood at a rate commensurate with the requirements of the metabolizing tissues, or can do so only at an abnormally elevated filling pressure. There are many specific disease processes that can lead to heart failure with a resulting difference in pathophysiology of the failing heart, such as the dilatation of the left ventricular chamber. Etiologies that can lead to this form of failure include idiopathic cardiomyopathy, viral cardiomyopathy, and ischemic cardiomyopathy.

The process of ventricular dilatation is generally the result of chronic volume overload or specific damage to the myocardium. In a normal heart that is exposed to long term increased cardiac output requirements, for example, that of an athlete, there is an adaptive process of ventricular dilation and myocyte hypertrophy. In this way, the heart fully compensates for the increased cardiac output requirements. With damage to the myocardium or chronic volume overload, however, there are increased requirements put on the contracting myocardium to such a level that this compensated state is never achieved and the heart continues to dilate.

The basic problem with a large dilated left ventricle is that there is a significant increase in wall tension and/or stress both during diastolic filling and during systolic contraction. In a normal heart, the adaptation of muscle hypertrophy (thickening) and ventricular dilatation maintain a fairly constant wall tension for systolic contraction. However, in a failing heart, the ongoing dilatation is greater than the hypertrophy and the result is a rising wall tension requirement for systolic contraction. This is felt to be an ongoing insult to the muscle myocyte resulting in further muscle damage. The increase in wall stress is also true for diastolic filling. Additionally, because of the lack of cardiac output, there is generally a rise in ventricular filling pressure from several physiologic mechanisms. Moreover, in diastole there is both a diameter increase and a pressure increase over normal, both contributing to higher wall stress levels. The increase in diastolic wall stress is felt to be the primary contributor to ongoing dilatation of the chamber.

Prior art treatments for heart failure fall into four general categories. The first being pharmacological, for example, diuretics. The second being assist systems, for example, pumps. Third, surgical treatments have been experimented with, which are described in more detail below. Finally, multi-site pacing contract the heart muscles at the same time.

With respect to pharmacological treatments, diuretics have been used to reduce the workload of the heart by reducing blood volume and preload. Clinically, preload is defined in several ways including left ventricular end diastolic pressure (LVEDP), or left ventricular end diastolic volume (LVEDV). Physiologically, the preferred definition is the length of stretch of the sarcomere at end diastole. Diuretics reduce extra cellular fluid which builds in congestive heart failure patients increasing preload conditions. Nitrates, arteriolar vasodilators, angiotensin converting enzyme inhibitors have been used to treat heart failure through the reduction of cardiac workload through the reduction of afterload. Afterload may be defined as the tension or stress required in the wall of the ventricle during ejection. Inotropes such as digoxin are cardiac glycosides and function to increase cardiac output by increasing the force and speed of cardiac muscle contraction. These drug therapies offer some beneficial effects but do not stop the progression of the disease.

Assist devices include, for example, mechanical pumps. Mechanical pumps reduce the load on the heart by performing all or part of the pumping function normally done by the heart. Currently, mechanical pumps are used to sustain the patient while a donor heart for transplantation becomes available for the patient. There are at least three surgical procedures for treatment of heart failure: 1) heart transplant; 2) dynamic cardiomyoplasty; and 3) the Batista partial left ventriculectomy. Heart transplantation has serious limitations including restricted availability of organs and adverse effects of immunosuppressive therapies required following heart transplantation. Cardiomyoplasty includes wrapping the heart with skeletal muscle and electrically stimulating the muscle to contract synchronously with the heart in order to help the pumping function of the heart. The Batista partial left ventriculectomy includes surgically remodeling the left ventricle by removing a segment of the muscular wall. This procedure reduces the diameter of the dilated heart, which in turn reduces the loading of the heart. However, this extremely invasive procedure reduces muscle mass of the heart.

SUMMARY OF THE INVENTION

The present invention pertains to a device and method for reducing mechanical heart wall muscle stress. Heart wall muscle stress is a stimulus for the initiation and progressive enlargement of the left ventricle in heart failure. Reduction in heart wall stress with the devices and methods disclosed herein is anticipated to substantially slow, stop or reverse the heart failure process, some or reverse the heart failure process, improve contractile function with decrease in isovolumetric contractions and improved isotonic shortening. Although the primary focus of the discussion of the devices and methods of the present invention herein relates to heart failure and the left ventricle, these devices and methods could be used to reduce stress in the heart's other chambers.

The devices and methods of the present invention are primarily external devices which need not necessarily penetrate the heart wall or transect a heart chamber. These devices can be used instead of, or in addition to, internal or transventricular devices. Unlike transventricular devices, however, avoidance of internal ventricular structures such as valves or chordae is not a concern. It is desirable to limit the size of the external devices to limit inflammatory response that may be created by implanting the device. Additionally, the weight of the device should be limited to reduced movement and forces which can induce inflammatory response or other negative physiologic responses as well. To limit the weight and size of the device, the devices can be constructed with materials with high strength to weight ratios and high stiffness to weight ratios. Size and weight interact to effect the stability of the device on the heart. The devices are preferably stabilized on the heart by tissue ingrowth, sutures, friction fit or the like.

The devices and methods of the present invention can reduce heart wall stress throughout the cardiac cycle including end diastole and end systole. Alternately they can be used to reduce wall stress during the portions of the cardiac cycle not including end systole. Those devices which operate throughout the cardiac cycle can be referred to as "full cycle" devices whereas those that do not operate to reduce wall stress during end stage systole can be referred to as "restrictive" devices.

BRIEF DESCRIPTION OF THE DRAWINGS

FIG. 1 is a perspective view of a heart wall tension reduction device in accordance with the present invention;

FIG. 2 is a generally horizontal cross section of the device of FIG. 1;

FIG. 3 is a view of an alternate embodiment of a heart wall tension apparatus in accordance with the present invention;

FIG. 4 is a generally horizontal cross sectional view of the device of FIG. 3;

FIG. 5 is a view of an alternate embodiment of a heart wall tension apparatus in accordance with the present invention;

FIG. 6 is a view of an alternate embodiment of a heart wall tension apparatus in accordance with the present invention;

FIG. 10 is a view of an alternate embodiment of a heart wall tension apparatus in accordance with the present invention;

FIG. 11 is a view of an alternate embodiment of a heart wall tension apparatus in accordance with the present invention;

FIG. 12 is a generally horizontal cross sectional view of the device of FIG. 11;

FIG. 13 is a view of an alternate embodiment of a heart wall tension apparatus in accordance with the present invention;

FIG. 14 a view of an alternate embodiment of a heart wall tension apparatus in accordance with the present invention;

FIG. 15 is a perspective view of the device of FIG. 14;

FIG. 16 is a view of an alternate embodiment of a heart wall tension apparatus in accordance with the present invention;

FIG. 25 is a view of an alternate embodiment of a heart wall tension apparatus in accordance with the present invention;

FIG. 26 is a view of an alternate embodiment of a heart wall tension apparatus in accordance with the present invention;

FIG. 27 is a view of an alternate embodiment of a heart wall tension apparatus in accordance with the present invention;

FIG. 28 is a view of an alternate embodiment of a heart wall tension apparatus in accordance with the present invention;

DETAILED DESCRIPTION OF THE INVENTION

Figure 7:
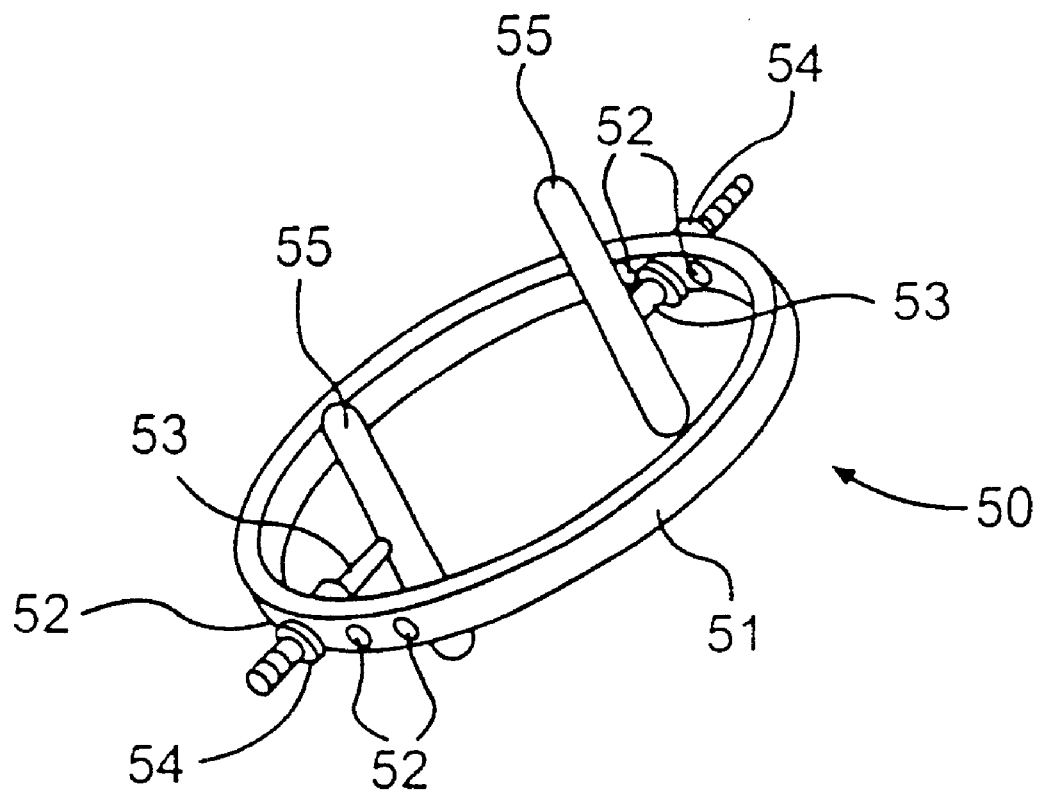
FIG. 7 is a view of an alternate embodiment of a heart wall tension apparatus in accordance with the present invention.

Referring now to the drawings wherein like reference numerals refer to like elements throughout the several views, FIG. 1 is a generally vertical view of human heart A having a left ventricle B and right ventricle C. Disposed on heart A is a heart wall stress reduction apparatus 10 including a band 12 disposed generally horizontally around heart A. Disposed between band 12 and heart A are generally ellipsoidal balloons 14. In FIG. 2, heart A is shown in context, in a generally transverse cross sectional view of a human torso. Heart A is shown disposed generally between left lung D and right lung E. In FIG. 2 it can be seen that band 12 retains balloon 14 with sufficient force to deform left ventricle B from a generally circular cross sectional configuration to a bi-lobe configuration. It is anticipated that device 10 could be adjusted for full cycle shape change of left ventricle B or be more loosely placed on the heart as a restrictive device, not creating a shape change at end systole. In addition to the bi-lobe configuration of FIG. 2, the shape change could also be of such a substantial magnitude that the chamber is substantially bifurcated by bringing the oppositely disposed heart walls into contact with each other.

Band 12 preferably does not substantially elongate under operational loads, but could be formed from material which deforms elastically under operational loading. Band 12 is preferably formed from a biocompatible material such as expanded PTFE or a polyester such as Dacron™. Balloon 14 could be a pre-inflated balloon filled with saline or curable polymer prior to placement between band 12 and heart A. Balloon 14 could also be inflated after placement between band 12 and heart A and then sealed by means known to those skilled in the art. It can be appreciated that balloons 14 need not, in fact, be balloons but could be solid or hollow ellipsoidal members made from biocompatible metals or plastics. Balloon 14 preferably includes an expanded PTFE or Dacron™ surface which has a pore size disposed toward heart A which would allow tissue ingrowth. It may be desirable to have a pore size of material covering band 12 and balloons 14 disposed away from the heart which does not promote tissue ingrowth, however. The pore size to promote tissue ingrowth is preferably between about 10 and about 100 microns and more preferably, between about 20 and about 40 microns. With respect to expanded PTFE, the internodal dimension is preferably between about 10 to about 100 microns and more preferably between about 20 to about 40 microns.

FIG. 3 is a generally vertical view of heart A. Disposed on heart A is an alternate heart wall stress reduction device 20 including a generally rigid frame 22. Frame 22 preferably includes generally horizontal cross members 24 and generally vertical cross members 26. Extending from cage 22 are struts 28 having one end connected to frame 22 and an opposite end connected to anchors 29. By adjusting the lengths of struts 28, pads 29 can engage left ventricle B to create a shape like that shown in FIG. 4.

Frame 22 is preferably made from a biocompatible metal or plastic and is substantially rigid during operational loading. Frame 22 could, however, be formed of a material which would allow elastic deformation during use. The materials used to form device 20 are preferably relatively light to enhance stability of device 28 on heart A. Light metals which could be used to form device include Co—Cr—Mo alloys, Co—Ni—Cr—Mo alloy (MP35N), carbon and titanium alloys (Ti-6AL-4V). In addition to plastics such as polyester, device 20 could be formed from composites such as carbon fibers/epoxy, polyester/epoxy, or amide fiber/epoxy, for example. Anchors 29 are preferably pad or disk shaped, atraumatic and include material coating having a pore size such as that described above with respect to device 10 which promotes tissue ingrowth. Additionally, sintered metal could create a pore size which would promote tissue ingrowth.

FIG. 5 is an alternate embodiment of a heart wall stress reduction device 30 disposed on heart A which is shown in a generally vertical orientation. Device 30 preferably includes a sock 31 formed from a porous mesh of biocompatible fabric such as polyester. Sock 31 preferably does not substantially stretch or elongate under operational loads. Sock 31 could, however, be made from a material which deforms elastically at operational loads. Disposed between sock 31 and heart A is an elongate bar 32. Bar 32 is preferably held against left ventricle B with sufficient force to create a shape change such as that shown in FIG. 2 when a second bar 32 is disposed between sock 31 and the posterior side of heart A. Sock 31 is preferably held in place on heart A by sutures. FIG. 6 is yet alternate embodiment 40 of a heart wall stress reduction device. Device 40 is similar to device 30 except that it includes a shell 42 which is substantially rigid under operational loads rather than a sock 31 and inwardly protruding members 40 rather than a bar 32. Shell 42 can be slipped over heart A to create a shape change similar to that shown in FIG. 2. Members 44 are thus preferably profiled such that they can be slid atraumatically over heart A to place device 40.

Device 40 is preferably made from those materials described with respect to device 20 above. The surface of protrusions 44 preferably include a surface which promotes tissue ingrowth as described above. Device 40 can be held in place on heart A by sutures placed through apertures (not shown) in shell 42.

FIG. 7 is yet another embodiment of a heart wall stress reduction device 50 in accordance with the present invention. Device 50 includes a preferably substantially rigid ring 51. Ring 51 could, however, be made from a material which deforms elastically under operational loads. Ring 51 preferably has a plurality of apertures 52 disposed circumferentially on opposite sides of ring 51. Extending through an aperture 52 on opposite sides of ring 51 are struts 53. Struts 53 can be extended inwardly from ring 51 by adjusting threaded fasteners 54. Threaded fasteners 54 are preferably provided on strut 53 such that strut 53 can be retained in place while acted upon by outward or inwardly directed forces. At the inward end of strut 53 is an elongate anchor or pad 55. It can be appreciated that ring 51 could be placed around heart A and the position of pads 55 adjusted such that a shape change of left ventricle B could be created similar to that shown in FIG. 2.

Device 50 could advantageously be made from those materials described with respect to device 20. Anchors 55 preferably include a porous surface which allows for tissue ingrowth as described above.

Figure 8:
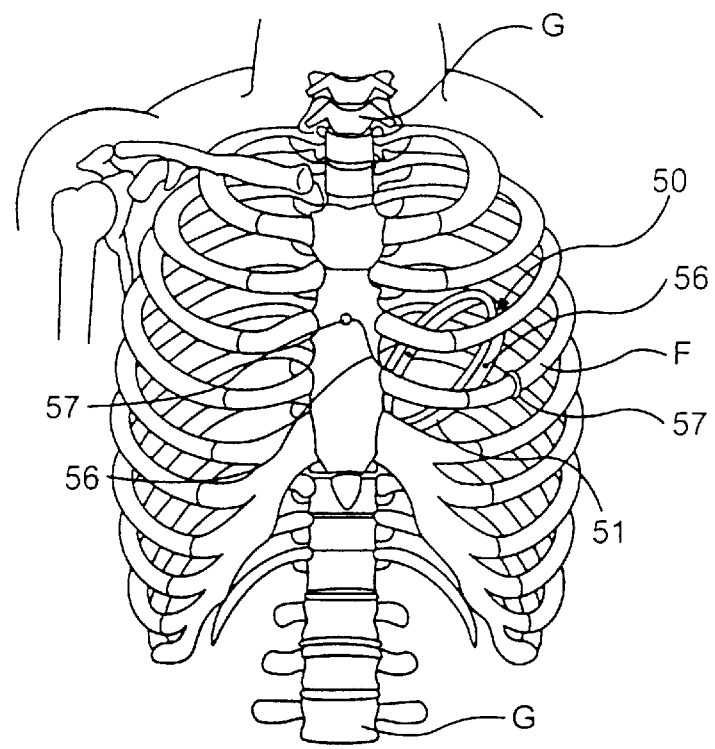
FIG. 8 is a view of the device of FIG. 7 connected to a skeleton of a patient.
Figure 9:
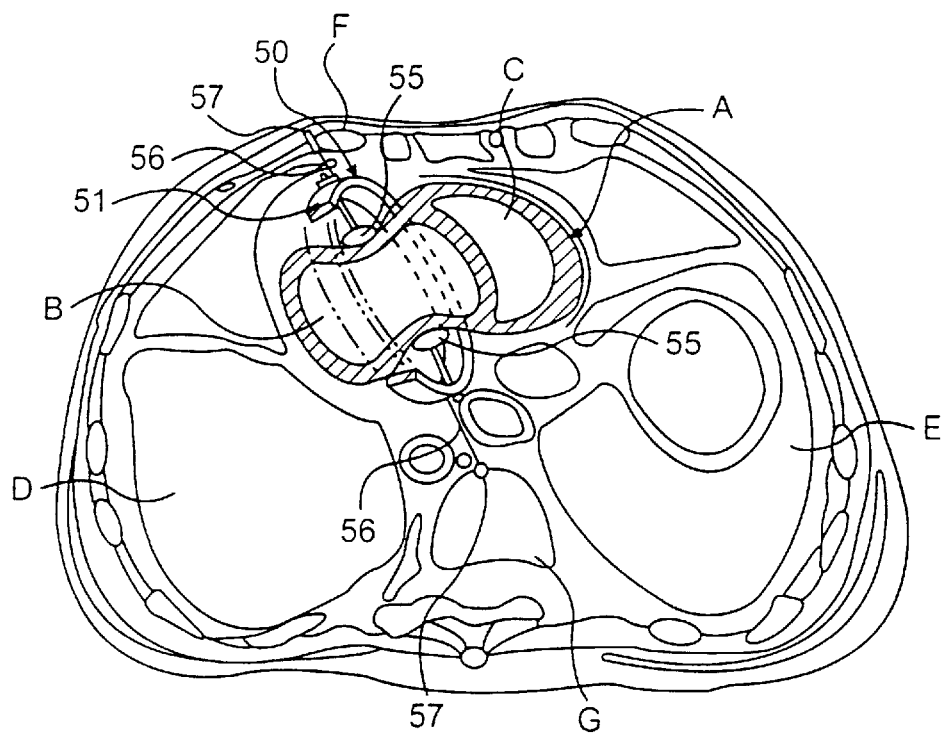
FIG. 9 is a generally horizontal cross sectional view of the device of FIG. 7 disposed within a patient.

FIG. 8 is a generally vertical view of the skeleton of a human torso. A device 50 is shown disposed within ribs F. Device 50 is held in position by a tether 56 anchored by a loop or bone screw 57 to ribs F and an oppositely disposed tether 56 and loop or bone screw 57 attached to spinal column G. FIG. 9 is a generally transverse cross sectional view taken through FIG. 8 of device 50 and short soft tissue organs including heart A and lungs D and F.

FIG. 10 is a vertical view of heart A. Disposed on heart A is an alternate embodiment 60 of a heart wall stress reduction device. Device 60 is a band shown wrapped generally horizontally around left ventricle B. Band 60 is preferably formed from polyester or other biocompatible plastic such as Dacron™. Band 60 preferably has an inwardly disposed surface which is porous to promote tissue ingrowth as described above. Band 60 preferably does not substantially elongate under operational loadings. Band 60 could, however, be formed from materials which elongate under operational loading. In addition to, or prior to tissue ingrowth band 60 could be held in place by, for example, sutures. Device 60 could be a closed loop or a loop having free ends which are buckled or fastened together by Velcro™ or other means known in the art (not shown).

Band 60 does not create a left ventricular shape change having a bi-lobe configuration in a horizontal cross section as shown in FIG. 2. Rather, band 60 forms a bi-lobe configuration in vertical cross section.

FIG. 1 is a vertical cross sectional view of heart A. Disposed on heart A is yet an alternate embodiment of a heart wall stress reduction device 65 in accordance with the present invention. Device 65 is substantially similar to device 60. Device 65 is, however, shown extending around the exterior of left ventricle B and placed through right ventricle C. Device 65 thus includes a band having free ends which are attachable after placement of the device through right ventricle C and around left ventricle B.

As can be seen in FIG. 12, device 65 does not create a horizontally bi-lobe configuration such as that shown in FIG. 2. Rather, device 65 creates a bi-lobe configuration of left ventricle B in a vertical cross sectional view.

FIG. 13 is a view of device 60 placed on heart A in a manner similar to that shown in FIG. 10, but used in conjunction with an additional elongate bar 62. Bar 62 can be similar to bar 32 shown in FIG. 5. It can be appreciated that if bar 62 is disposed between device 60 and heart A, and a second bar 62 is similarly disposed on the posterior side of heart A, a bi-lobed shape change can be created in a generally horizontal cross section of left ventricle B. It can also be appreciated that device 60 will also create a bi-lobed shape change on left ventricle B in a generally vertical cross section.

FIG. 14 is a generally vertical view of heart A. Disposed on right ventricle B of heart A are two generally C-shaped, alternate heart wall stress reduction devices 70. Device 70 preferably includes a generally C-shaped cross member 71 having two oppositely disposed ends. On opposite ends of cross members 71 are preferably disposed anchors 72. Anchors 72 are preferably disc or pad shaped and have an innerly disposed porous surface to allow tissue ingrowth as described above. As shown in FIG. 14, two C-shaped devices 70 can be used together to form a bi-lobe shape change of left ventricle B in a manner similar to that shown in FIG. 2.

Cross member 71 is preferably made from a malleable metal which can be bent prior to placement such that the desired spacing is obtained between oppositely disposed anchors 72. It is possible that the spacing of pad 72 could be adjusted while device 70 is placed on the heart, but pre-placement spacing adjustment is preferred. In addition to malleable materials or metals, cross member 71 could also be formed from plastics or composites such as those described above with respect to device 20. FIG. 15 is a perspective view of device 70 not including heart A.

FIG. 16 is yet alternate embodiment of a heart wall stress reduction apparatus 75 in accordance with the present invention. Device 75 is essentially similar to device 70, except that cross member 76 is shown in a band shape and anchors 77 are generally elongate. Elongate anchors may be desirable for both device 75 and 70 to create a bilobe shape change over a greater generally vertical extent of left ventricle B.

Figure 17:
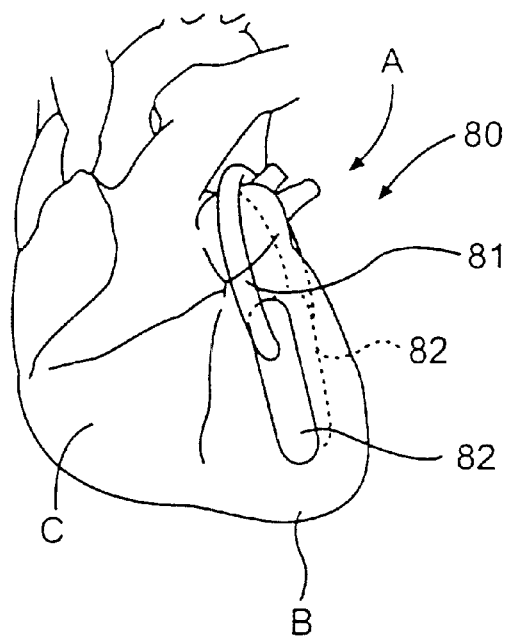
FIG. 17 is a view of an alternate embodiment of a heart wall tension apparatus in accordance with the present invention.
Figure 18:
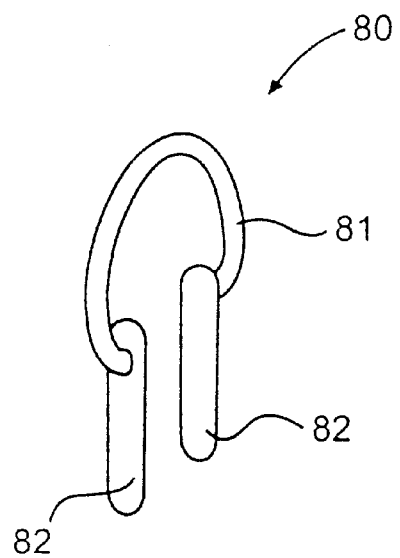
FIG. 18 is a perspective view of the device of FIG. 17.

FIG. 17 is a generally vertical view of heart A. Yet another alternate embodiment of a heart stress reduction device 80 is shown disposed on heart A. Device 80 is similar to device 70, except that it includes elongate anchors 82 and a cross member 81 disposed generally in alignment with the longitudinal axis of anchor 82. This allows cross member 81 to rest on an upper surface of heart A to resist gravitational displacement of device 80 from heart A. FIG. 18 is a view of device 80 apart from heart A.

As an alternative to a C-shaped device such as device 70 which is preferably adjusted or sized prior to placement on heart A, devices such as those shown in FIG. 19–28 can readily be adjusted in place on the heart. The devices of FIGS. 19–28 include mechanical mechanisms for adjusting anchor spacing. Each of these devices could be positioned in heart A to create a shape change similar to that of FIG. 2. The devices of FIGS. 19–28 are preferably made from light biocompatible metal and/or plastics. The anchors or pads preferably have a porous heart engaging surface to promote tissue ingrowth.

Figure 19:
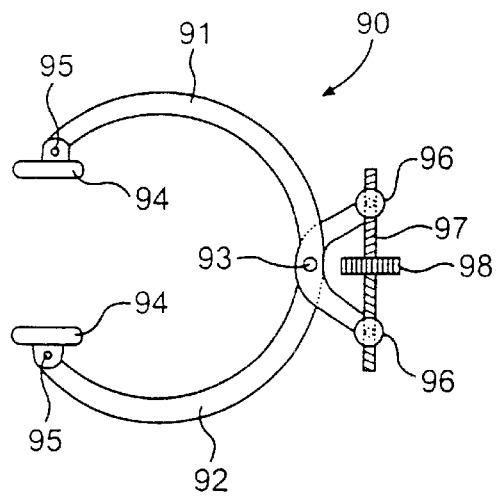
FIG. 19 is a view of an alternate embodiment of a heart wall tension apparatus in accordance with the present invention.

FIG. 19 is a view of yet another alternate embodiment of a heart wall stress reduction device 90 in accordance with the present invention. Device 90 includes two oppositely disposed arms 91 and 92 pivotally attached by a pin 93 to form a C-shape. Disposed at the free ends of each arm 91 and 92 is an anchor or anchor pad 94 pivotally attached to arms 91 and 92 by pins 95. Pivotally attached to the opposite ends of arms 91 and 92 are internally threaded members 96 into which is threaded a rod 97. Disposed along, and fixably attached to rod 97 is a thumb wheel 98 for rotating rod 97. Rod 97 is preferably flexible enough that as it is rotated to draw the ends of arms 91 and 92 together, it can be deformed such that wheel 98 will move to the right as upper member 96 pivots counterclockwise and lower member 96 pivots clockwise.

Figure 20:
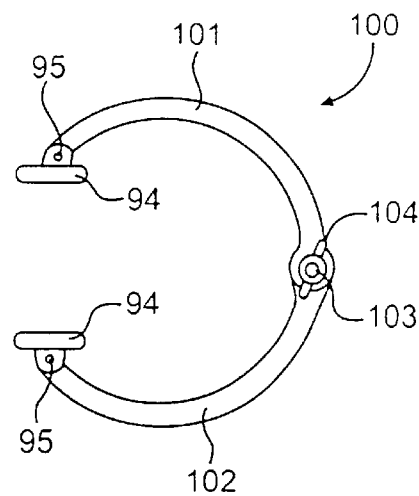
FIG. 20 is a view of an alternate embodiment of a heart wall tension apparatus in accordance with the present invention.

FIG. 20 is a view of yet an alternate embodiment 100 of a C-shaped heart wall stress reduction device. Device 100 includes arms 101 and 102. Disposed at the free ends of arms 101 and 102 are pads 94 pivotally connected thereto by pins 95. At the opposite ends of arms 101 and 102, they are joined by a bolt 103 and wing nut 104. Wing nut 104, when loosened will allow arms 101 and 102 to pivot around bolt 103. Wing nut 104 can be tightened to fix the relative position of arms 101 and 102 when the desired spacing of pads 94 has been achieved.

Figure 21:
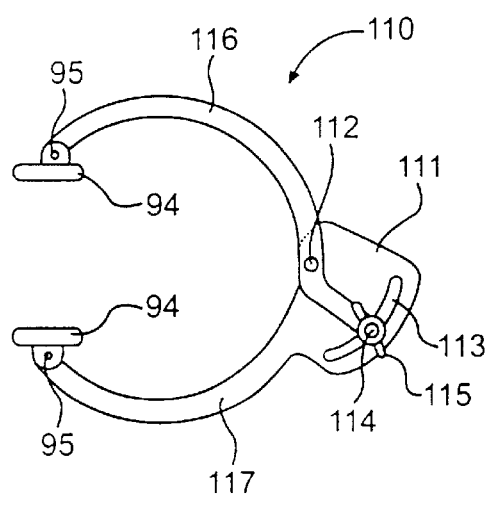
FIG. 21 is a view of an alternate embodiment of a heart wall tension apparatus in accordance with the present invention.

FIG. 21 is a view of yet an alternate embodiment 110 of a C-shaped heart wall stress reduction device. Device 110 is similar to device 100 except that oppositely disposed arms 116 and 117 are cantilevered beyond their pivotable attachment point at pin 112 to a bolt 114 and a wing nut 115. Arm 117 includes a plate 111 having an arc-like aperture 113 formed therein. Bolt 114 extends through aperture 113 and arm 116 such that when wing nut 115 is loose, bolt 114 can slide in aperture 113 to rotate arm 116 about pin 112 to adjust the spacing between pads 94. When the desired spacing is achieved, wing nut 115 can be tightened to fix the relative position of arms 116 and 117.

Figure 22:
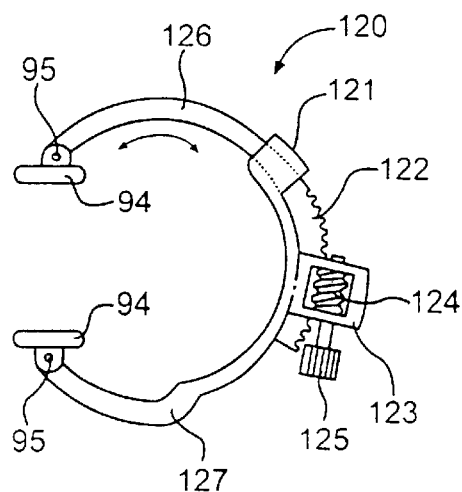
FIG. 22 is a view of an alternate embodiment of a heart wall tension apparatus in accordance with the present invention.

FIG. 22 is a view of yet another alternate embodiment of a generally C-shaped heart wall stress reduction device 120. Device 120 includes two oppositely disposed arms 126 and 127. Pads 94 are pivotally attached by pins 95 to the free ends of arms 126 and 127. The opposite end of arm 126 is slidably disposed through a receiving housing 121 at the opposite end of arm 127. The end of arm 127 extending through housing 121 includes teeth 122. Disposed between housing 121 and pad 94 and along arm 127 is a screw gear housing 123 which positions the threads of a screw gear 124 between teeth 122. Gear 124 includes a shaft having a thumb knob 125 attached thereto. Knob 125 can be used to rotate screw 124 to engage successive teeth 122 to move arm 126 relative to arm 127 in the directions shown by the arrow. Thus, in this manner, arm 126 can be moved to adjust the spacing between pads 94.

Figure 23:
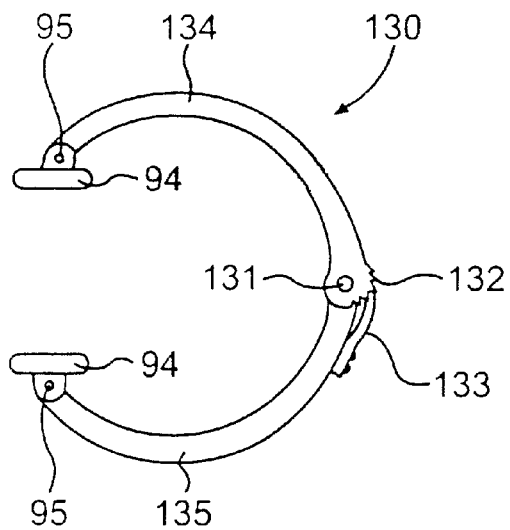
FIG. 23 is a view of an alternate embodiment of a heart wall tension apparatus in accordance with the present invention.

FIG. 23 shows yet another alternate embodiment of a generally C-shaped heart wall stress reduction device 130 in accordance with the present invention. Device 130 is similar to device 100 except for oppositely disposed arms 134 and 135 are pivotable about pin 131 and fixable in position by ratchet teeth 132 of arm 134 and an elongate member 133 connected to arm 135. Ratchet teeth are sloped such that as arm 134 is pivoted about pin 131 to bring pads 94 closer together, member 133 rides over successive teeth 132. If, however, it is attempted to rotate 134 in the opposite direction, teeth 132 are sloped to engage member 133 and resist the rotation of arm 134 about pin 131. Member 133 can be pulled away from teeth 132 to allow arm 134 to be pivoted in a clockwise direction.

Figure 24:
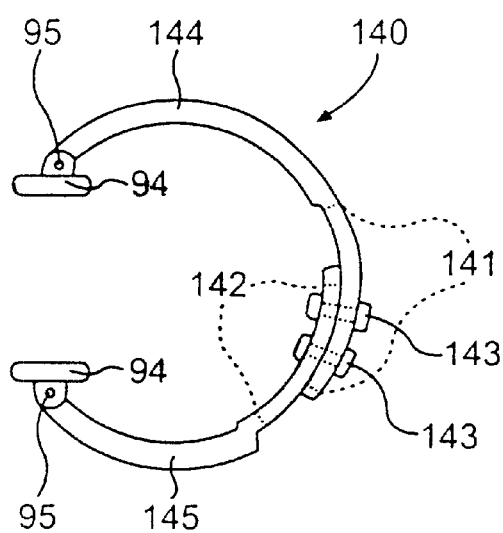
FIG. 24 is a view of an alternate embodiment of a heart wall tension apparatus in accordance with the present invention.

FIG. 24 is a view of yet an alternate embodiment of a generally C-shaped heart wall tension reduction device 140 in accordance with the present invention. Device 140 includes oppositely disposed arms 144 and 145. Anchors 94 are pivotally attached by pins 95 to the free ends of arms 144 and 145. The opposite ends of arms 144 and 145 include slots 141 and 142. As shown in FIG. 24, where slots 141 and 142 overlap, nut and bolt assemblies 143 are disposed therethrough. As can be appreciated, if nut and bolt assemblies 143 are loosened they will be free to slide within slots 141 and 142 such that the ends of arms 144 and 145 disposed opposite pads 94 can be slid over each other to adjust the distance between pads 94. Once the desired distance between pads 94 is obtained, nut and bolt assemblies can be tightened to fix the relative position of arms 144 and 145.

FIG. 25 is a view of yet an alternate embodiment of a generally C-shaped heart wall stress reduction device 150 in accordance with the present invention. Device 150 includes two oppositely disposed arms 153 and 154. Pads 94 are pivotally attached by pins 95 to the pins of arms 153 and 154. The opposite end of arm 153 is slidably received within an aperture of a receiving housing 151 connected to the opposite end of arm 154. A set screw 152 is threaded into housing 151 such that when set screw 152 is loose, arm 153 can slide within housing 151 to vary the distance between pads 94. Once the desired distance between pads 94 has been obtained, set screw 152 can be tightened to engage arm 153 and fix its position relative to arm 154.

FIG. 26 is a view of yet an alternate generally C-shaped heart wall stress reduction apparatus 160 in accordance with the present invention. Device 160 includes a generally C-shaped arm 161 which has two oppositely disposed free ends. Pads 94 are pivotally connected by pins 95 to each of the free ends. Disposed along the interior arc of arm 161 are eyelets 163. Disposed through eyelets 163 is a line or cable 164 having two oppositely disposed ends fixably attached to opposite pads 94. A more centrally located portion of line 164 is at least partially wrapped around a spool 165. Spool 165 is rotatably connected to a generally central portion of member 161. A knob 166 is connected to spool 165 to allow rotation thereof It can be appreciated that if spool 165 is rotated into the paper in the direction of the arrow, that the spacing between pads 94 will decrease as line 164 is pulled through eyelets 163 toward spool 165. It can be appreciated that if spool 165 is rotated in an opposite direction, pads 94 will move apart to the extent that member 161 is biased to expand outwardly. The position of spool 165 can be fixed when the desired spacing of pads 94 is obtained by tightening a set screw 167 disposed adjacent knob 166.

FIG. 27 is a view of yet an alternate embodiment of a generally C-shaped heart wall tension apparatus 170. Heart wall tension reduction apparatus 170 includes two oppositely disposed arms 171 and 172. Disposed at the free end of arms 171 and 172 are anchors 173 and 174, respectively. Anchors 173 and 174 can be anchor pads each having a disc-like heart engaging surface similar to that of anchor 94. The portion of anchors 173 and 174 opposite the disc-shaped portion includes socket shaped portions 175 and 176, respectively. These socket shaped portions 175 and 176 are shaped similarly to that of the socket portions of ball and socket joints. Disposed along the length of arms 171 and 172 are ball and socket members 179. Each member 179 includes a generally ball shaped or hemispherical end 181 and a complimentary concaved socket end 180. As shown, a series of members 179 are placed ball end to socket end to form each arm 171 and 172. The final ball end 181 of each arm 171 and 172 is disposed within sockets 175 and 176 respectively of anchors 173 and 174, respectively.

Each member 179 includes a longitudinal lumen extending therethrough. A line 182 extends through successive of these lumens in arms 171. A line 183 extends through arm 172 in a similar fashion. Lines 182 and 183 are free to move within the lumens but are fixably attached at their ends to anchors 173 and 174, respectively. The opposite ends of lines 182 and 183 pass over pulleys 185 and are connected to a spool or takeout reel 186 which in turn is pivotally connected to a central housing 184. Housing 184 includes oppositely disposed ball portions 188 and 189, which engage the sockets of the adjacent members 179. A knob 187 is provided to rotate spool 186. If spool 186 is rotated in the direction shown by the arrow, lines 182 and 183 will be drawn toward spool 186, which in turn will draw the adjacent ball and socket ends toward each other. When the force exerted by lines 182 and 183 is sufficient, friction between adjacent ball and socket ends will hold arms 171 and 172 in any position in which they have been placed. Thus, when the desired spacing between anchors 173 and 174 is obtained and lines 182 and 183 tightened, a set screw 177 can be tightened to retain spool 186 in position to maintain the spacing between anchors 173 and 174. Not only can the spacing between anchors 173 and 174 be controlled in this manner, but the shape of the arm can be altered along its length to be straight or arcuate to conform to the shape of the heart.

FIG. 28 is a view of an alternate arm configuration 190 which could be used in a generally C-shaped heart wall stress reduction apparatus. The principle of its operation would be similar to that of the device of FIG. 23, except that a plurality rather than one ratcheting member would be provided. By providing a plurality of ratcheting members, the shape of the arm can be altered along its length to be relatively straighter, or more arcuate depending upon the degree to which the various members are ratcheted with respect to each other.

Arm 190 includes a plurality of ratcheting members 191. A first end 192 of each member 191 is pivotally connected to the opposite end 193 of each member 191 by a pin 194. Each member can be rotated about pins 194 in the direction shown by the arrows. Teeth 195 are disposed at each end 193 to engage a ratcheting arm 196 extending from end 193 toward end 192. It can be appreciated that member 196 should be flexible enough that a physician can ratchet arm 196 over teeth 195 until the desired rotational position is obtained. The arms should also, however, be rigid enough that during normal operational heart loadings, member 126 remains between the teeth 129 selected by the physician.

Figure 29:
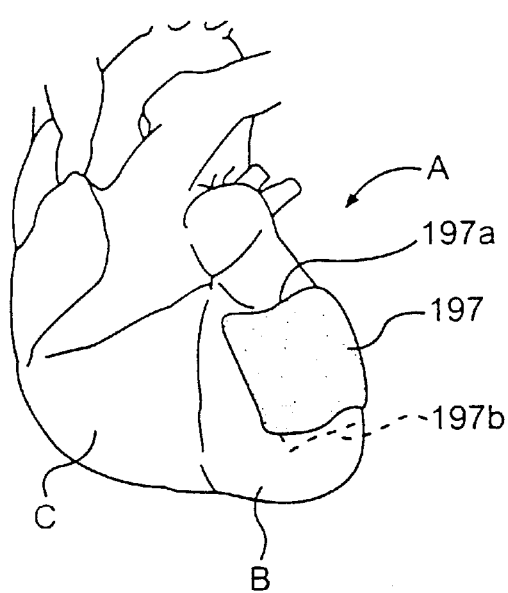
FIG. 29 is a view of an alternate embodiment of a heart wall tension apparatus in accordance with the present invention.

FIG. 29 is a generally vertical view of heart A. Yet another alternate embodiment of a heart wall stress reduction device 197 is shown on left ventricle B. Device 197 is preferably a sheet which has been wrapped around a portion of left ventricle B. The sheet includes a generally vertical elongate concave trough 197a on the anterior side of left ventricle B and a similar trough 197b on the posterior side of left ventricle B. The base of the trough can be made to engage opposite sides of the ventricle to create a bi-lobe shape similar to that shown in FIG. 2.

The sheet is preferably formed in place on heart A to create the troughs 197a and 197b. The sheet can be formed from an epoxy or a composite including two or more of the following: epoxy, Dacron™, silicone or UV curable adhesive. The sheet, if made using a curable adhesive or epoxy should be placed prior to curing such that the sheet can be readily formed in a shape similar to that shown in FIG. 29. During the curing process, the sheet can be held in place using one or more generally C-shaped heart wall tension reduction devices such as those shown in FIGS. 14–28.

The sheet material used to form device 197 could also be a malleable metal such as stainless steel. If a metal such as stainless steel were used to form the sheet, it could be bent to form a shape similar to that shown in FIG. 29 prior to placement on the heart or while being placed on heart A.

Figure 30:
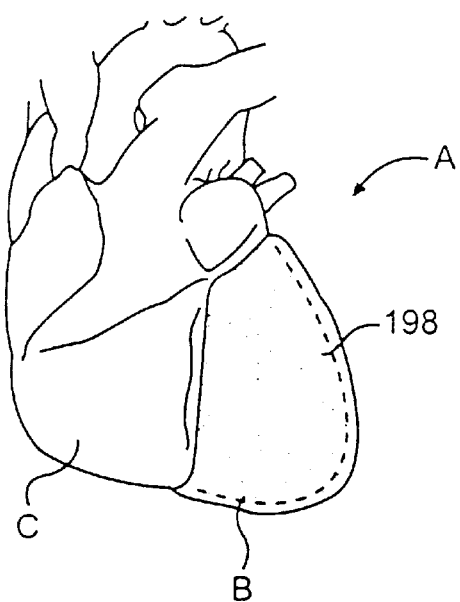
FIG. 30 is a view of an alternate embodiment of a heart wall tension apparatus in accordance with the present invention.

FIG. 30 is a generally vertical view of a heart A. Yet another embodiment of a heart wall stress reduction device 198 is shown disposed on left ventricle B. As shown in FIG. 30, device 198 has a shell or helmet shape which substantially surrounds left ventricle B. Device 198 could be formed from materials in a manner described above with respect to device 197. In particular, troughs could be created in opposite sides of shell 198 to create a bi-lobe shape similar to that shown in FIG. 2.

Figure 31:
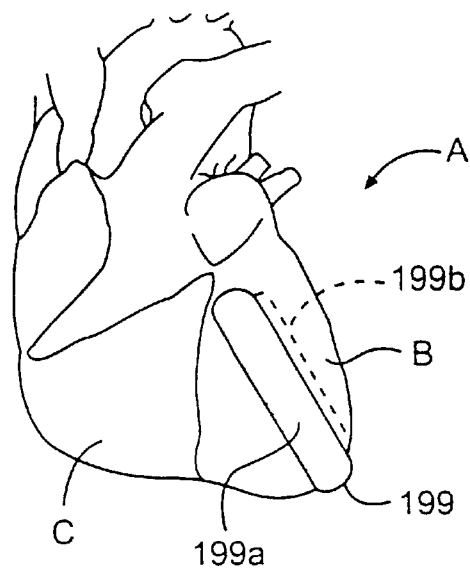
FIG. 31 is a view of an alternate embodiment of a heart wall tension apparatus in accordance with the present invention.

FIG. 31 is a view yet another embodiment of a heart wall stress reduction device 199 shown disposed on left ventricle B of heart A. Device 199 has a generally U-shape including an anterior arm 199a and a posterior arm 199b. Arms 199a and 199b can be positioned on left ventricle B to create a bi-lobe shape of left ventricle B similar to that shown in FIG. 2. The materials and methods used to make and place device 199 are similar to those used to make and place device 197 of FIG. 29.

Figure 32:
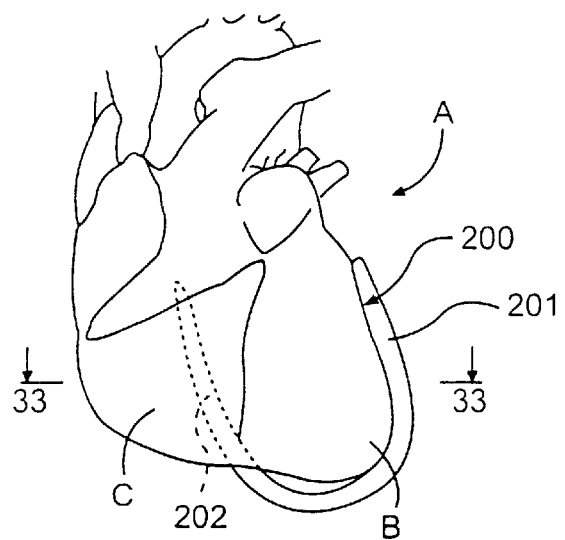
FIG. 32 is a view of an alternate embodiment of a heart wall tension apparatus in accordance with the present invention.
Figure 33:
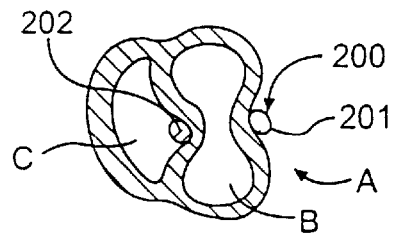
FIG. 33 is a generally horizontal cross sectional view taken from FIG. 32.

FIG. 32 is a view of yet another alternate embodiment of a heart wall stress reduction device 200. Device 200 is generally C-shaped and includes an arm 201 and arm 202. As can be appreciated by reference to FIG. 33, which is a generally horizontal cross sectional view taken from FIG. 32, arm 22 is disposed within right ventricle C and arm 201 is disposed opposite to give left ventricle B a generally bi-lobe cross sectional shape.

Device 200 can be formed from a biocompatible metal or plastic. Device 200 can include a porous coating or surface to promote tissue ingrowth as described above and/or be held in place on heart A by sutures through apertures (not shown) in device 200.

Figure 34:
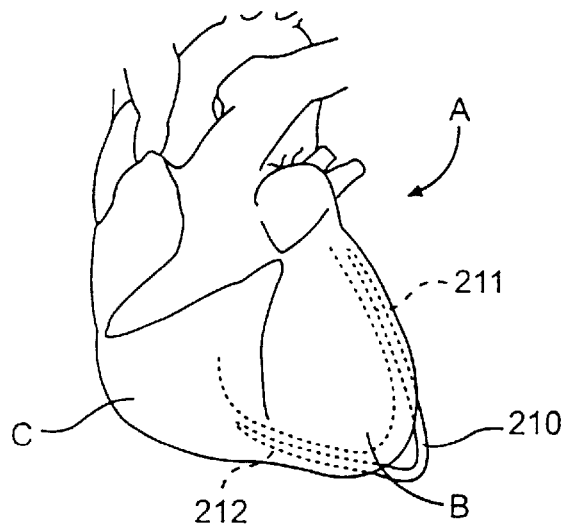
FIG. 34 is a view of an alternate embodiment of a heart wall tension apparatus in accordance with the present invention.

FIG. 34 is a yet another alternate embodiment of a heart wall stress reduction device 210 shown disposed within heart A. Device 210 has a generally V-shape and includes an arm 211 and another arm 212. Device 210 can be made from a biocompatible metal or plastic. Device 210 can be held in place by sutures extending through apertures in device 210 (not shown) and/or by providing a porous surface which promotes tissue ingrowth as described above. The free ends of arms 211 and 212 are preferably sufficiently narrowed such that they can be advanced through and disposed within the ventricular walls and/or septum rather than alongside the wall and/or septum. The device can be configured to, and placed to form a bi-lobe cross sectional shape of left ventricle B such as that shown in FIG. 2 or 32.

Figure 35:
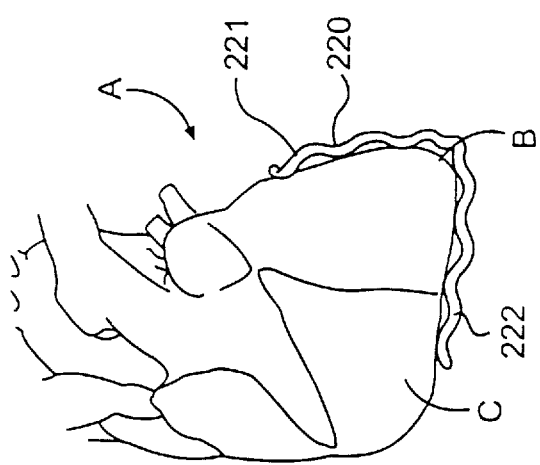
FIG. 35 is a view of an alternate embodiment of a heart wall tension apparatus in accordance with the present invention.

FIG. 35 is a view of yet another embodiment of a heart wall stress reduction device 220 shown disposed on the right ventricle of heart A. Device 220 has a generally V-shape and includes an arm 221 and an opposite arm 222. Arms 221 and 222 have a generally multiple wave or ungulating shape. When placed on the surface of the heart, the wave shape focuses pressure on the heart wall at space locations rather than continuously. It is anticipated that by spacing the contact points of device 220 that there will be a limited interruption of coronary blood flow as a result of impingement of the device on heart A.

Device 220 is preferably made from similar materials to that of device 210. Device 220 can be configured and placed on a heart to form a bi-lobe cross sectional shape of left ventricle B in a shape similar to that shown in FIG. 2.

Figure 36:
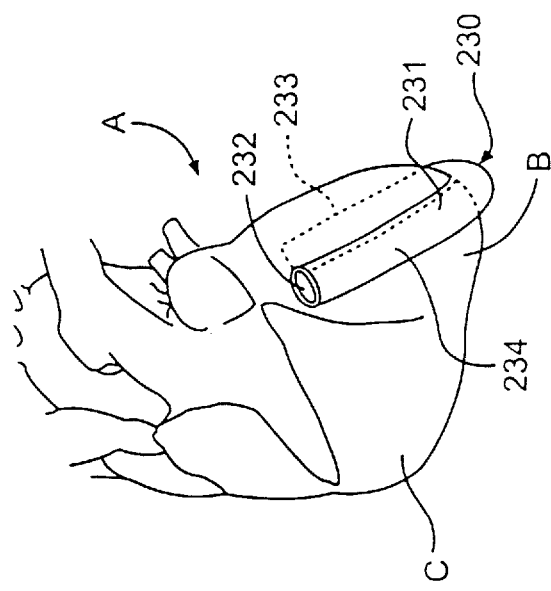
FIG. 36 is a view of an alternate embodiment of a heart wall tension apparatus in accordance with the present invention.

FIG. 36 is a view of yet an alternate embodiment of a heart wall stress reduction device 230 in accordance with the present invention. Device 230 has a generally U-shape including an arm 233 and opposite arm 234. Device 230 preferably is formed from a tubular shell 231 and can be made from a biocompatible material such as PTFE. Disposed within tube 231 is a curable material such as epoxy urethane 232. Similarly to device 199 of FIG. 31, device 30 is placed on the heart prior to curing of material 232 within tube 231. Arms 233 and 234 can be positioned to create a bi-lobe cross sectional shape of left ventricle B such as that shown in FIG. 2. One or more heart wall tension reduction devices similar to those shown in FIGS. 14–28 can be used to temporarily hold arms 233 and 234 in place until material 232 has cured.

Figure 37:
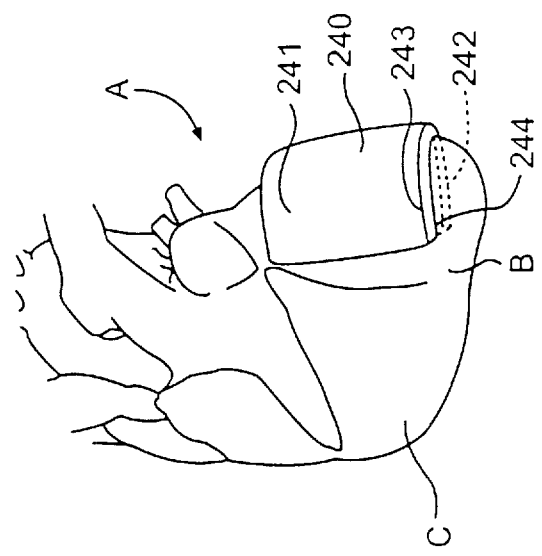
FIG. 37 is a view of an alternate embodiment of a heart wall tension apparatus in accordance with the present invention.

FIG. 37 is a view of yet an alternate embodiment 240 of a heart wall stress reduction device in accordance with the present invention. Device 240 is formed from a sheet configured in a generally U-shape having a side 241 and an opposite side 242 shown disposed on the anterior and posterior sides of left ventricle B. Device 240 is preferably formed from a malleable sheet 243. An inner sheet 244 of expanded PTFE or other material can be disposed on the inside surface of device 240 to allow tissue ingrowth. Sheet 243 could, however, also be sintered to promote tissue ingrowth and inner sheet 244 not used. Device 240 could be bent to obtain the desired configuration prior to placement on heart A or bent in place on heart A to obtain the desired cross section of left ventricle B. With device 240, a generally bi-lobe shape such as that shown in FIG. 2 can be obtained in a configuration similar to that of device 197 of FIG. 29. Additionally, device 240 could be placed without troughs formed in opposite sides such as those of device 197, but rather with generally planar arms 241 and 242. In such a case, if generally planar arms 241 and 242 are brought into a generally parallel configuration, left ventricle B can be compressed to create generally oblong, generally horizontal cross sectional configuration.

As shown herein the various heart wall stress reduction devices and methods have been applied to form a bi-lobe configuration of the left ventricle. It can be appreciated that the devices and methods disclosed herein can also be used to create three or more lobes in the left ventricle. Additionally, the heart wall stress reduction devices and methods disclosed herein can also be used to change the shape of the remaining chambers of the heart in addition to the left ventricle. The external device as disclosed herein could also be used in conjunction with transventricular heart wall stress reduction devices. In such instance, both devices could be full cycle, restrictive, or one of the devices could be full cycle and the other restrictive. It can also be appreciated that the rotational positioning of the device about the heart can be varied to create a shape change between posterior and anterior anchors or between lateral anchors.

Numerous characteristics and advantages of the invention covered by this document have been set forth in the foregoing description. It will be understood, however, that this disclosure is, in many respects, only illustrative. Changes may be made in details, particularly in matters of shape, size and ordering of steps without exceeding the scope of the invention. The invention's scope is, of course, defined in the language in which the appended claims are expressed.

What is claimed is:

1. A method for reducing heart wall stress in a heart chamber, comprising the steps of:

providing a passive device having a first heart engaging surface, a second heart engaging surface, and a member interconnecting the surfaces; and placing the first and second surfaces on the wall of the chamber to deflect the heart wall proximate at least one of the heart engaging surfaces, while the interconnecting member is disposed externally of the heart, wherein the first and second heart engaging surfaces are configured to promote tissue ingrowth.

2. The method in accordance with claim 1, wherein the deflection appears concave from outside the chamber.

3. The method in accordance with claim 1, wherein the deflection results in an inflection point along the wall of the heart.

4. The method in accordance with claim 1, wherein the first heart engaging surface includes a balloon.

5. The method in accordance with claim 1, wherein the first heart engaging surface includes an elongate pad.

6. The method in accordance with claim 1, further comprising the step of attaching the device to a bone.

7. The method in accordance with claim 1, wherein the first and second heart engaging surfaces are porous.

8. The method in accordance with claim 1, further comprising the step of adjusting the distance between the surfaces.

9. The method in accordance with claim 1, wherein the member is malleable.

10. The method in accordance with claim 1, wherein the member is cast in place on the heart.

* * * * *